United States Patent [19]

Baker et al.

[11] Patent Number: 4,705,518
[45] Date of Patent: * Nov. 10, 1987

[54] ARTIFICIAL SPHINCTER APPARATUS AND METHOD

[75] Inventors: Charles D. Baker, Lehi; Owen D. Brimhall; Charles R. Galway, both of Salt Lake City, all of Utah

[73] Assignee: University of Utah Research Institute, Salt Lake City, Utah

[*] Notice: The portion of the term of this patent subsequent to Nov. 19, 2002 has been disclaimed.

[21] Appl. No.: 799,846

[22] Filed: Nov. 18, 1985

Related U.S. Application Data

[63] Continuation-in-part of Ser. No. 367,533, Apr. 12, 1982, Pat. No. 4,553,271, which is a continuation-in-part of Ser. No. 194,528, Oct. 6, 1980, abandoned.

[51] Int. Cl.$^4$ ............................ A61F 2/08; A61F 2/04
[52] U.S. Cl. ...................................... 623/14; 128/1 R; 128/346; 623/66
[58] Field of Search ............... 128/DIG. 25, 1 R, 325, 128/326, 303 R, 346; 138/45; 623/14, 66

[56] References Cited

U.S. PATENT DOCUMENTS

| | | | |
|---|---|---|---|
| 2,434,835 | 1/1948 | Colley | 138/45 |
| 2,569,850 | 10/1951 | Falconer | 93/77 |
| 3,705,580 | 12/1972 | Gauthier | 128/79 |
| 3,974,854 | 8/1976 | Kurpanek | 623/2 X |
| 4,092,010 | 5/1978 | Carlson, Jr. | 251/4 |
| 4,194,848 | 3/1980 | Kingsford | 401/5 |
| 4,217,899 | 8/1980 | Freier | 128/283 |
| 4,360,007 | 11/1982 | Levy et al. | 128/1 R |
| 4,401,107 | 8/1983 | Haber et al. | 128/1 R |
| 4,551,862 | 11/1985 | Haber | 623/14 |
| 4,553,271 | 11/1985 | Baker | 623/14 |
| 4,612,011 | 9/1986 | Kautzky | 623/2 |

FOREIGN PATENT DOCUMENTS 2717607 10/1978 Fed. Rep. of Germany ... 728/DIG. 25

Primary Examiner—Richard J. Apley
Assistant Examiner—Alan W. Cannon
Attorney, Agent, or Firm—Workman, Nydegger & Jensen

[57] ABSTRACT

An artificial sphincter apparatus and method, the artificial sphincter including a pair of parallel, coaxially mounted rings with at least one ring rotatable relative to the other. Optionally the rings are capable of being split open at their circumference and reclosed for mounting about a living tissue conduit for which surgical severing is not recommended. A plurality of circumferentially mounted tie members extend between the rings and are drawn laterally toward the center of the sphincter, narrowing a passageway therethrough, upon relative rotation between the rings. This action is capable of gently constricting a living tissue conduit within the passageway using a combination of rotational and circumferentially localized discrete radially compressive forces to control the flow of biological materials within the living tissue conduit. A cell impervious thin flexible tubular membrane envelopes the sphincter to isolate it from the immediate environment. The membrane has a central waist portion which fits within the openings in the rings and ends which fold outwardly around the sphincter for sealing together at the outer circumference thereof. In one embodiment of the invention such a membrane, when provided with compliant folds in the central waist portion thereof, replaces the plurality of tie members as a closure means for narrowing the passageway through the sphincter. Operation of the artificial sphincter after its implantation is effected by a number of disclosed remote and proximate actuation means.

43 Claims, 27 Drawing Figures

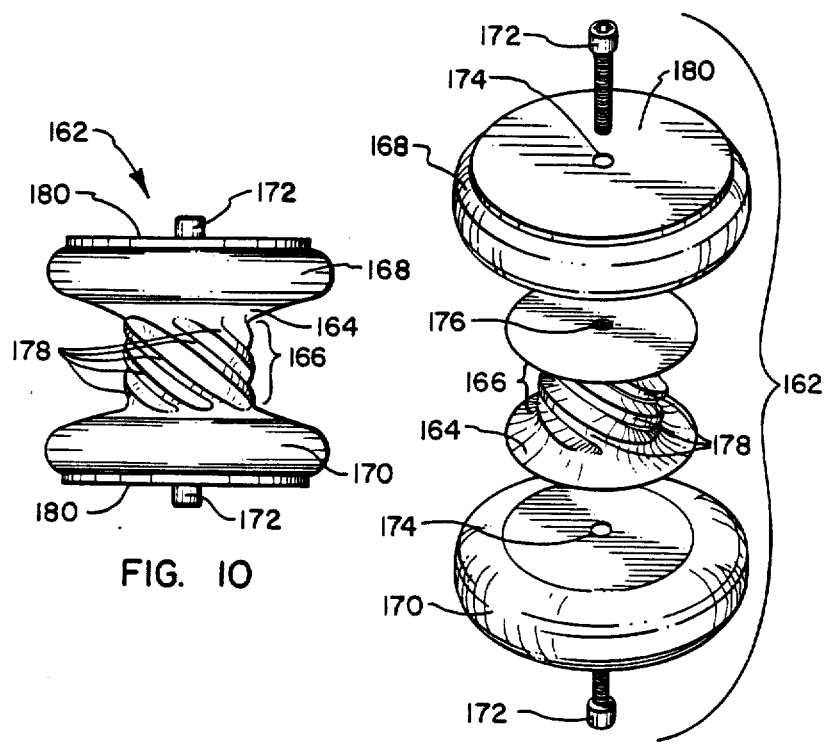
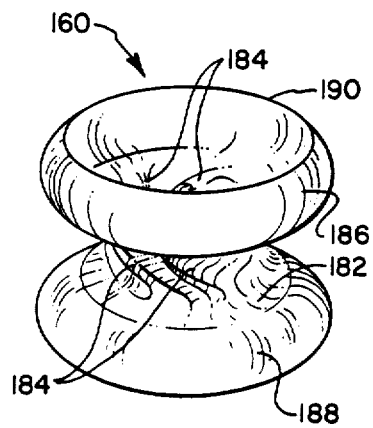
FIG. 10
FIG. 11
FIG. 12
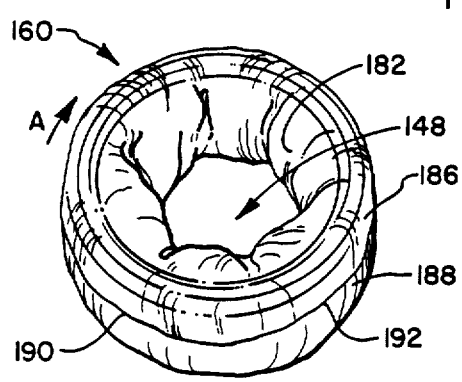
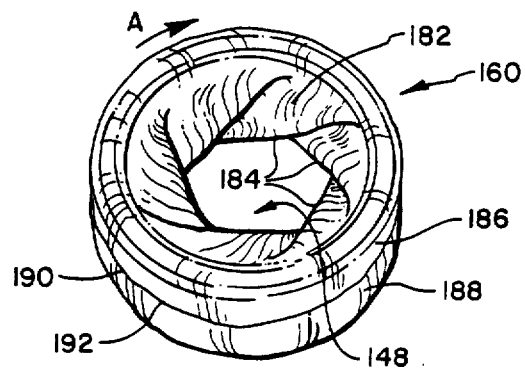
FIG. 13A
FIG. 13B
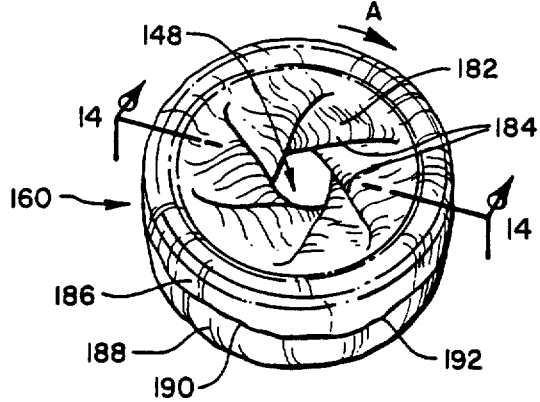
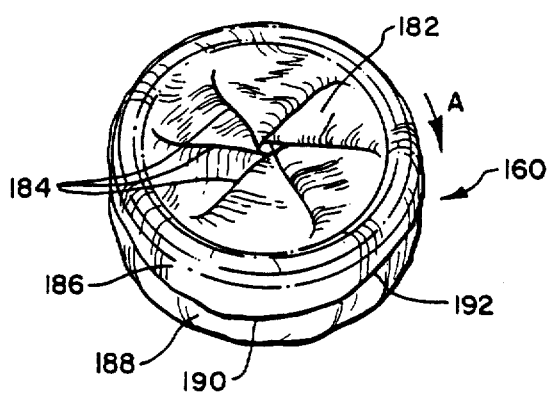
FIG. 13C
FIG. 13D

ARTIFICIAL SPHINCTER APPARATUS AND METHOD

RELATED APPLICATIONS

This application is a continuation-in-part application of copending U.S. patent application Ser. No. 367,533 filed Apr. 12, 1982, and issued on Nov. 19, 1985, as U.S. Pat. No. 4,553,271, which is itself a continuation-in-part application of U.S. patent application Ser. No. 194,528 filed Oct. 6, 1980, now abandoned, as to both of which one of the joint inventors named herein was the named applicant.

BACKGROUND OF THE INVENTION

1. The Field of the Invention

This invention relates to a construction apparatus and method having application in the medical arts, and more particularly to an artificial sphincter capable of gently constricting a living tissue conduit to control the flow of biological materials therein without causing damage to living tissue of the conduit. Constriction of the living conduit is achieved in the apparatus and method of this invention through a combination of rotational and localized discrete radially compressive forces.

2. The Background Art

In the field of medical research and health care delivery, it is frequently necessary to clamp a living tissue conduit or otherwise stop the flow of biological materials (such as blood, urine, or stool) through such a conduit. Clamps which are well-known in the art generally involve two jaw members which transversely crimp the vessel to shut off the flow therein. It is also well known, however, that such vessels, have irregular wall thicknesses and corresponding irregularities in the inner wall surface. Thus a clamp having jaws which move with a parallel clamping action must clamp the vessel tightly enough to seal the thinnest portion of the irregular wall surface in order to prevent leakage past the clamp. Accordingly, if a conventional clamp of this type is used for a significant period of time, pressure necrosis of the underlying living tissue of the vessel results.

While many procedures have been adapted to alleviate this particular problem, it would be a significant advancement in the art to provide a construction apparatus and method for gently constricting the flow of biological materials through a living tissue conduit which minimizes the changes of damaging the living tissue of such a vessel through pressure necrosis. Numerous applications call for a constricting movement, such as that present in a sphincter-type muscle, wherein muscular constriction radially narrows an open structure. Various other flow control devices could also benefit from axially oriented constricting movement.

A constriction or crimping apparatus disclosed in Falconer (U.S. Pat. No. 2,569,850) includes a plurality of rods mounted circumferentially around an axial opening parallel the axis thereof. A tube inserted in the opening is crimped by twisting the rods about the axis. Other constricting devices are shown in the patents of Colley (U.S. Pat. No. 2,434,835); Carlson, Jr. (U.S. Pat. No. 4,092,010); and Kingsford (U.S. Pat. No. 4,194,848). These devices, however, use entirely different operative mechanisms from that of the present invention.

SUMMARY OF THE INVENTION

The present invention involve a construction apparatus which employs the basic principle of a sphincter-type muscle. The apparatus includes two, parallel and axially mounted rings interconnected by a plurality of annularly arrayed tie members extending between the two rings. The rings may optionally be afforded with structure permitting them to be split open at their circumference and closed again to facilitate encirclement of a living tissue conduit of the type which should not be surgically severed when implanting the apparatus. Relative rotation between the rings causes the tie members to be angularly and tangentially brought toward the axis of the constriction apparatus. The type and length of the tie members and the spatial separation and diameter of the rings determines the characteristics of the constricting force imparted by the apparatus.

In addition, the artificial sphincter of the present invention includes structure which facilitates successful implantation and long term operation of such a device. In accordance with one aspect of the present invention as embodied and broadly described herein, an artificial sphincter is provided with a cell-impervious means for isolating the device from its surrounding environment. A thin flexible tubular membrane having a narrowed central portion dimensioned to fit within the central opening of the artificial sphincter is provided in addition with radially flared end portions for wrapping about the artificial sphincter and sealing to each other at the outer circumference of the device. The walls of the narrowed central portion of the membrane are formed into a plurality of compliant folds which permit a limited amount of rotation of either end of the membrane without producing significant tension in the walls of the central portion.

In another aspect of the present invention, a thin flexible tubular membrane is disclosed which serves to replace the tie members described above for gently constricting a living tissue conduit with a combination of rotational and circumferentially localized discrete radially compressive forces. Each of the radially flared end portions of the membrane are attached to one of the two rotatable rings to obtain this result.

In yet another aspect of the present invention, actuator means are provided for rotating the two rings relative to one another using controls remote from or proximate to the device once implanted. As provided in various embodiments of the present invention, such actuation means include, for example, remote cable and remote hydraulic actuation, as well as a means for actuating the device through its direct manipulation after subcutaneous implantation.

Accordingly, one object of the present invention is to provide an improved apparatus and method for gently constricting a living tissue conduit such that flow of biological materials with the living tissue conduit may be controlled without causing significant pressure necrosis to the living tissue of the conduit.

An additional objective of the present invention is to provide an improved artificial sphincter as described above which is capable of use to constrict a living tissue conduit which is not symmetrical or which should not be surgically severed when implanting the artificial sphincter.

Another object of the present invention is to provide an artificial sphincter which constricts a living tissue conduit to control the flow of biological materials therewithin through the application thereto of a combination of rotational and circumferentially localized discrete radially compressive forces.

One object of this invention is to provide a constriction apparatus wherein the quality of the constricting force may be selectively predetermined through the selection of a variety of device parameters.

Yet another object of this invention is to provide a novel constriction apparatus wherein the area of constriction may be determined by selection of the diameter and spatial separation of the two ring members.

Another object of this invention is to provide an artificial sphincter suitable for implantation by virtue of its being isolated from the surrounding environment in a cell-impervious membrane which prevents cell intrusion or growth into the device and fouling of its operating mechanisms.

Another objective is to provide an artificial sphincter having the operative mechanisms thereof activated either through direct manipulation of the implanted device or through use of control means remote from the site of implantation.

Additional objects and advantages of the invention will be set forth in the description which follows, and in part will be obvious from the description, or may be learned by the practice of the invention. The objects and advantages of the invention may be realized and obtained by means of the instruments and combination particularly pointed out in the appended claims.

BRIEF DESCRIPTION OF THE DRAWINGS

The invention will be described with additional specificity and detail through the use of the accompanying drawings in which:

FIG. 10 is an elevation view of a mandrel used to fabricate a suitable membrane for enveloping the device shown in FIG. 8;

FIG. 11 is an exploded perspective view of the mandrel shown in FIG. 10;

FIG. 12 is a perspective view of a membrane fabricated using the mandrel of FIGS. 10 and 11;

FIGS. 13A-13D are a sequence of perspective views of the membrane of FIG. 12 enclosing the device of FIG. 8 with components thereof in positions corresponding to FIGS. 9A-9D;

DESCRIPTION OF THE PREFERRED EMBODIENTS

Figure 1:
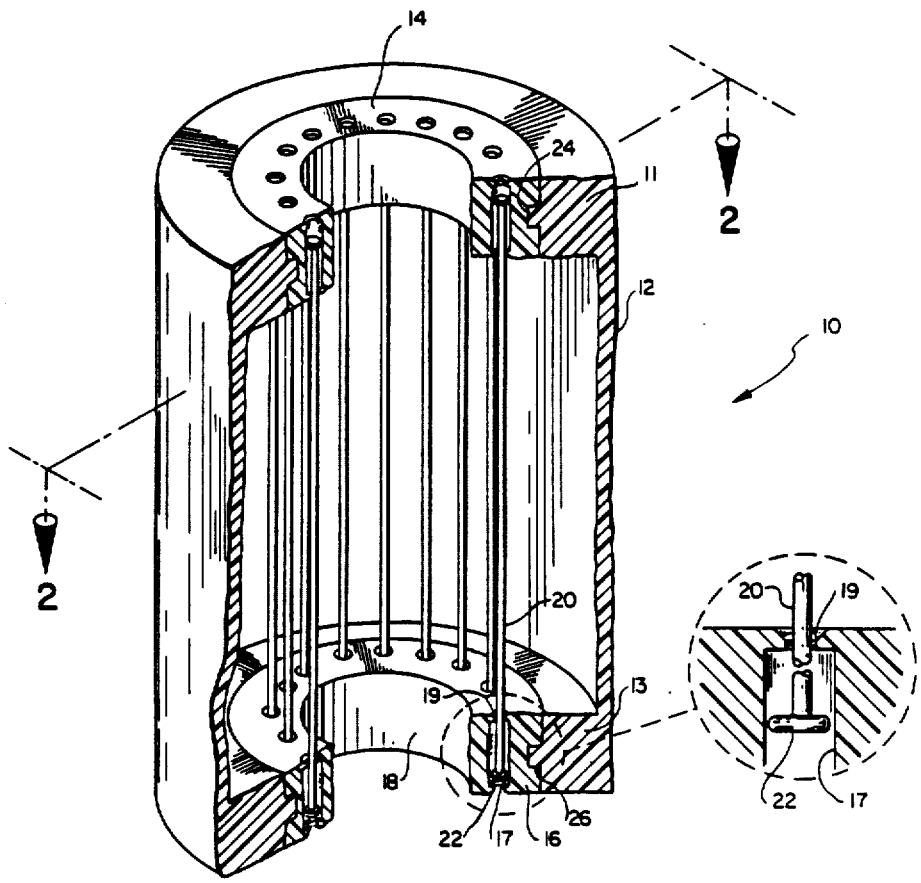
FIG. 1 is a perspective view of a first embodiment of the constriction apparatus of this invention with a portion broken away and an enlarged detail view to reveal internal construction.

Referring now more particularly to FIG. 1, a first preferred embodiment of the constriction apparatus of this invention is shown generally at 10 to include a hollow support column 12 configurated as a right cylinder and rotatably supporting a pair of spaced, coaxial ring members 14 and 16 in parallel relationship. Mounts 11 and 13 at each end of support column 12 rotatably support ring members 14 and 16, respectively, and hold the same therein in their respective relationships with mating, circular bearings 24 and 26, respectively.

Circular bearings 24 and 26 are shown herein as constituting an annular undercut in the respective ring members 14 and 16 cooperating with an internal shelf on the respective mounts 11 and 13. Clearly, however, circular bearings 24 and 26 may be of any suitable configuration to provide the appropriate frictional and support relationship between the respective ring member 14, 16 and corresponding mount 11, 13 therefor.

Rings 14 and 16 are coaxial and form a throughbore 18 through which an object to be constricted (not shown) may be placed and constricted by the inward movement of tie members 20, as will be discussed more fully hereinafter. Tie members 20 are shown as semi-rigid rods in this illustrated embodiment. Nevertheless, tie members 20 can be fabricated from any suitable material to incorporate desired characteristics into constriction apparatus 10. For example, tie members 20 may be fabricated from a flexible material or even an elastic material. Tie members 20 are mounted at each end in ring members 14 and 16 in a limited, slidable and rotatable relationship.

With respect to the enlarged view of a portion of FIG. 1, the end of a tie member 20 is shown extending through a countersunk throughbore 19 into a bore 17. A head 22 prevents tie member 20 from being pulled through countersunk throughbore 19. The length of bore 17 is selectively predetermined so that there is sufficient longitudinal movement of tie members 20 relative to ring members 14 and 16 to accommodate the relative movement of the ends of tie member 20 when ring members 14 and 16 are rotated relative to each other.

Figure 2:
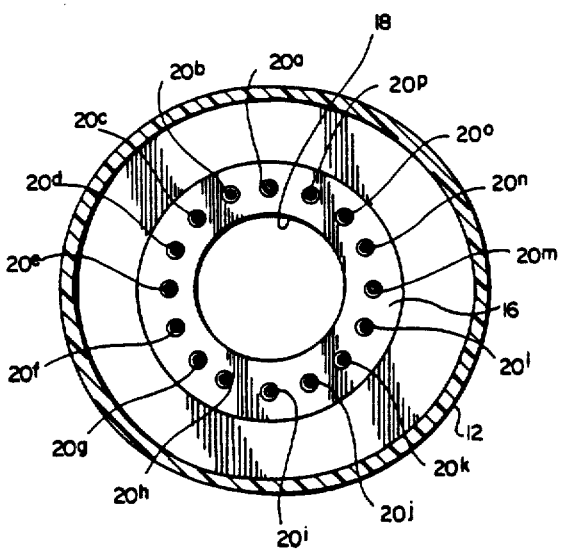
FIG. 2 is a cross-section taken along line 2—2 of FIG. 1.
Figure 3:
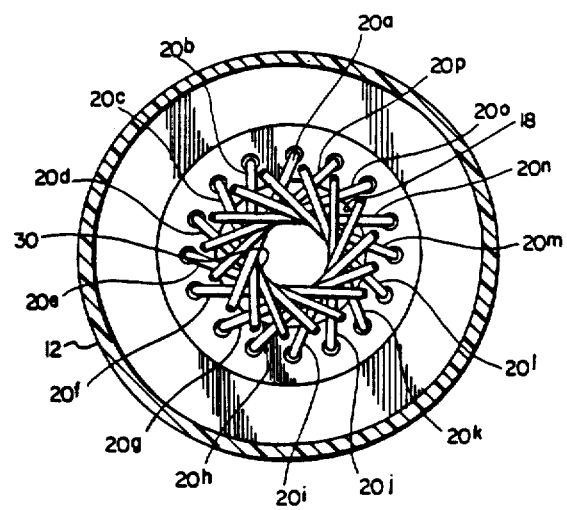
FIG. 3 is the cross-sectional view of FIG. 2 showing a relative rotation of the rings to illustrate the orientation and constricting movement of the tie members thus obtained.

For example, and with particular reference to FIGS. 2 and 3, a plurality of tie members 20a-20p are shown mounted in ring member 16 in an annular array around throughbore 18. With particular reference to FIG. 3, the view shown is as though ring member 14 (FIG. 1) has been rotated counterclockwise, thereby causing each of tie members 20a–20p to be moved angularly from a position perpendicular to the plane of the drawing to an angle relative to the axis of constriction apparatus 10, while simultaneously bringing tie members 20a–20p together in a combination of rotation and constricting movement toward the center of throughbore 18.

If viewed from the side, the tie members exhibit a profile generally corresponding to a pair of end-to-end cones having a generally frustoconical configuration with the area of constriction at the center of tie members 20a–20p. The area of constriction is determined by several factors including, for example, the length of the tie members 20a–20p relative to the diameter of ring members 14 and 16, the diameter of the annular array of tie members 20a–20p on ring members 14 and 16, the relationship thereof with the length of support of column 12, and spatial separation of ring members 14 and 16.

An additional factor affecting the length of the constriction surface relates to the flexibility or "softness" of tie members 20a–20p. For example, tie members 20a–20p shown herein are illustrated as essentially semi-rigid rods so that the constriction movement of tie members 20a–20p toward the axis of constriction apparatus 10 will be generally limited to a theoretical maximum of a 180° relative rotation in either direction between ring member 14 and ring member 16.

However, the theoretical maximum of 180° in either direction of relative rotation between ring members 14, 16 will not be achieved due to the individual diameters of each of tie members 20a–20p and the relative stiffness thereof. These factors together inhibit tie members 20a–20p to a constriction wherein the sides of tie members 20a–20p are in contact at the axis of constriction of apparatus 10. The resulting amount of rotation in either direction of relative rotation of ring members 14, 16 is thus somewhat less than 180°.

Tie members 20a–20p can, however, be selectively fabricated from a suitable, flexible or otherwise "soft" material, or even an elastic material having a predetermined degree of elasticity to accommodate relative rotation between ring member 14 and ring member 16 through more than 180°. Such relative rotation of ring members 14, 16, would result in a corresponding spiral twisting of tie members 20a–20p upon each other, thereby lengthening the area of constriction by tie members 20a–20p.

Figure 4:
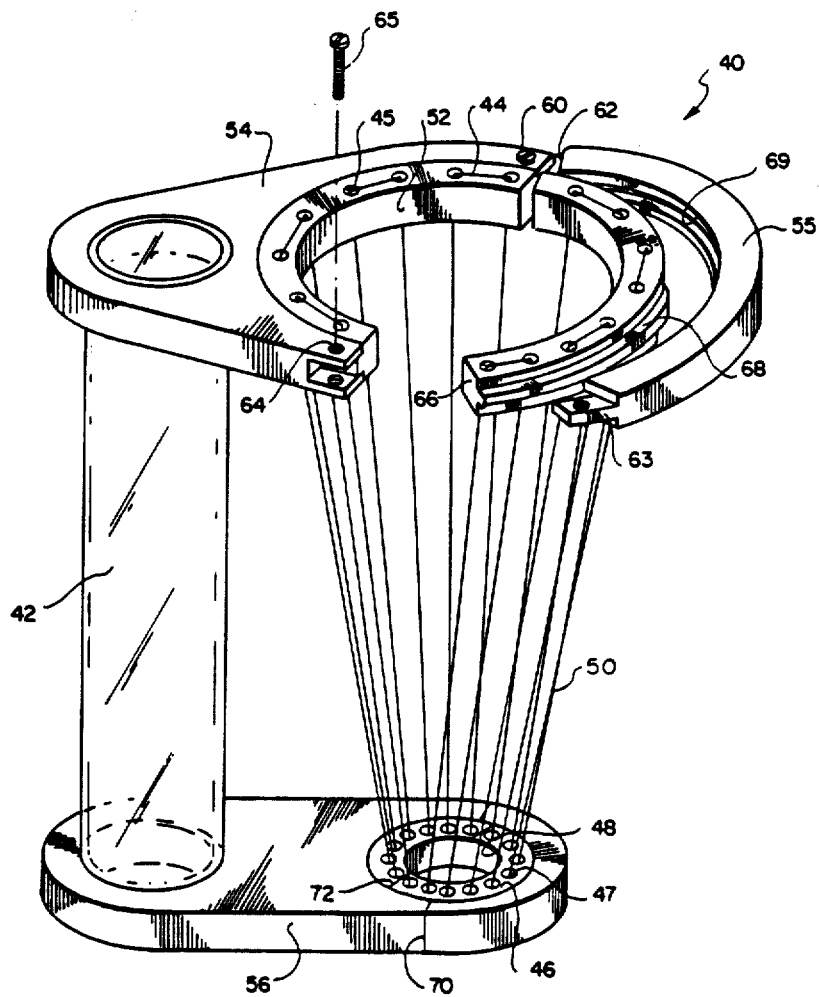
FIG. 4 is a perspective view of a second embodiment of the constriction apparatus of this invention.

Referring to FIG. 4, a second preferred embodiment of the constriction apparatus of this invention is shown which is responsive to the medical reality that several types of living tissue conduits to be constricted by an artificial sphincter according to the present invention may not, in contrast to the colon for example, be severed to facilitate implantation. Such an artificial sphincter 40 includes an upper ring member 44 supported in a mount 54 parallel and coaxial to a lower ring member 46 supported in a mount 56. As will be readily observed from FIG. 4, lower ring member 46 need not be of a diameter identical to that of upper ring member 44. In FIG. 4 lower ring member 46 has a diameter smaller than that of upper ring member 44. It will be understood that the point of constriction for constriction apparatus 40 will be nearer to ring member 46 than to ring member 44 by reason of the relative diameters of ring members 44 and 46. The relative sizes of ring members 44 and 46 have been somewhat exaggerated in FIG. 4 to more clearly illustrate the subject matter disclosed.

Upper ring member 44 is interconnected to lower ring member 46 by a plurality of tie members 50. Tie members 50 are configured as a plurality of cords interwoven through a plurality of throughbores 45 in upper ring member 44 and a plurality of corresponding throughbores 47 in lower ring member 46. Tie members 50 thereby form a conical throughbore through constriction apparatus 40.

Each of ring members 44 and 46 are configured as split ring members, so that each may be opened along corresponding joinders 66 and 72, respectively. Ring member 44, for example, is configured as a split ring retained by a tongue 68 in a groove 69 of the surrounding mount 55. Mount 55 is hinged at hinge point 60 and adapted to be interconnected through a bolt 65 joining a tongue 63 to a corresponding bracket 64. A similar joint for mount 56 is illustrated schematically as joint 70. The configuration of ring members 44 and 46 is such to accommodate opening of the ring members at joinders 66 and 72, respectively, to thereby encircle a living tissue conduit which whould not be surgically severed with constriction apparatus 40. Thereafter, the split ring members may be closed, interlocked in the respective mounts, and rotated relative to each other to thereby impart a combination of rotational and constricting force to the object thus engaged. This split-ring feature of the present invention can be incorporated into all embodiments to be described subsequently.

Mounts 54 and 56 are rigidly supported in parallel relationship by an offset support column 42. While support member 42 is shown in FIG. 4 as an external support means, constriction apparatus 10 (FIG. 1) or constriction apparatus 40 (FIG. 4) could be selectively interchanged with respect to support member 12 (FIG. 1) and support member 42 (FIG. 4) to thereby selectively locate the area of constriction produced by the constricting apparatus of this invention, either internally or externally of the support system thereof. In either configuration, the relative distance of the respective ring members is maintained during rotation of the rings relative to each other, so as to impart the desired combination of rotational and constricting forces to the object, encircled thereby.

Figure 5:
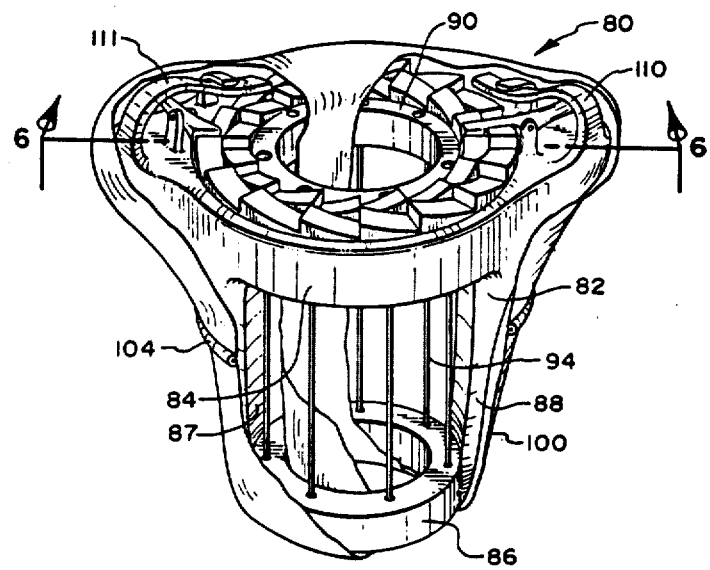
FIG. 5 is a perspective view of an artificial sphincter incorporating the apparatus of this invention, portions being broken away to reveal internal construction.
Figure 6:
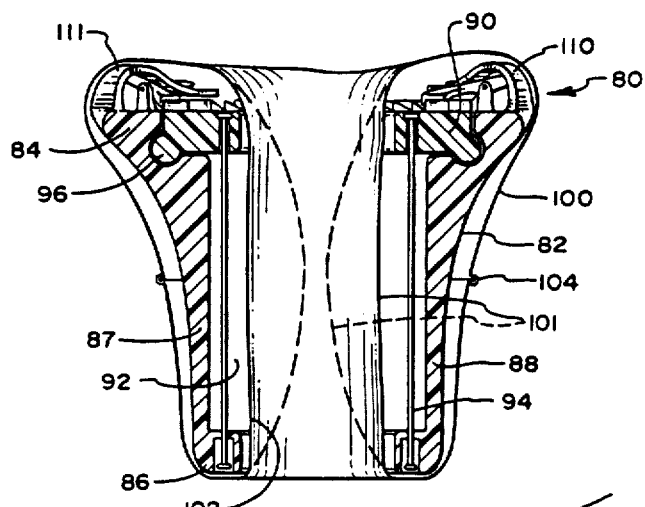
FIG. 6 is a cross-sectional view taken along line 6—6 of FIG. 5.
Figure 7:
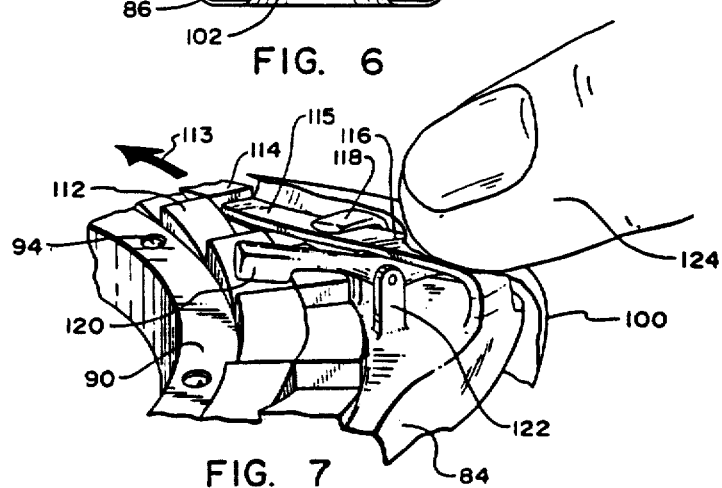
FIG. 7 is a fragmentary enlargement of a portion of FIG. 5 showing a portion of a finger in order to demonstrate operation of one method of actuating the embodiment of the artificial sphincter shown.

Referring now more particularly to FIGS. 5–7, the constriction apparatus of this invention is shown incorporated into an artificial sphincter 80. Artificial sphincter 80 is constructed with a basal framework 82 having an upper ring support 84 mounted to a lower ring 86 by a pair of support columns 87 and 88. Lower ring 86 is stationary while upper ring support 84 has rotatably mounted therein an upper ring 90. Upper ring 90 is rotatable in a plane parallel to lower ring 86, so as to provide the desired relative rotation between upper ring 90 and lower ring 86.

A plurality of tie members 94 are mounted circumferentially to each of upper ring 90 and lower ring 86 to thereby create an iris-like constrictive action of a throughbore 92, as discussed above with respect to the embodiments shown in FIGS. 1–4. Upper ring 90 also includes an annular detent 96 which fits within a cooperating annular groove in upper ring support 84. The dimensions and materials of construction of upper ring 90 and upper ring support 84 are such that detent 96 is held in a snap-fit relationship in upper ring support 84.

Since artificial sphincter 80 is intended for implantation, all of the materials of construction intended to be in contact with living tissue are fabricated from readily available, biocompatible materials. Alternatively and preferentially, the entire artificial sphincter apparatus 80 is enclosed in a fluid-impervious, flexible, biocompatible membrane 100 in order to minimize cell growth on or fouling of the components of the aritficial sphincter.

Membrane 100 is configured as a generally tubular member having a diametrally reduced waist 101 adapted to reside within and form a lumen 102 through the hollow throughbore 92 of artificial sphincter 80. The ends of tubular member 100 are diametrally enlarged and have matching diameters so that each may be folded outwardly over the respective ends of the artificial sphincter 80 and brought together in a joinder 104 circumferentially around the exterior of artificial sphincter 80. By this technique, artificial sphincter 80 is completely isolated within the envelope of membrane 100.

Rotation of upper ring 90 causes tie members 94 to constrict lumen 102 and correspondingly, a section of an organ, such as a small bowel, colon, blood vessel, uretha, or stomach portion passing therethrough. In this process, tie members 94 are moved inwardly in an iris-like constrictive action similar to that shown in FIG. 3, and lumen 102 within diametrically reduced waist 101 of membrane 100 is stretched in the area between upper ring 90 and lower ring 86 in accommodation thereto (dashed lines). Accompanying this stretching is a degree of rotational tension applied by tie members 94 to the same area of membrane 100.

Rotation of upper ring 90 is accomplished by movement of actuator mechanisms 110 and 111 on each side of artificial sphincter 80. Since the operation of actuator mechanisms 110 and 111 is identical, with the exception of the direction of rotation of upper ring 90, only the operation of the right-hand side of actuator mechanism 110 will be discussed.

Attention is particularly directed to FIG. 7 wherein actuator mechanism 110 is shown greatly enlarged for ease of presenting the detail and describing the operation thereof. Upper ring 90 forms a support for tie members 94, the ends of two of which can be seen in FIG. 7. Upper ring 90 also includes an inner ratchet 112 and an outer ratchet 114. Actuator mechanism 111 cooperates with inner ratchet 112 to rotate upper ring 90 in a clockwise direction, while actuator mechanism 110 cooperates with outer ratchet 114 to operate upper ring 90 in a counterclockwise direction, as shown schematically by arrow 113.

Actuator mechanism 110 includes a resilient arm 116 formed as an integral part of upper ring support 84 and held by a stop 118 in a position above but generally parallel to the respective ratchet, in this case, outer ratchet 114. The configuration of stop 118 and the arm 116 is selected so that the resilience of arm 116 holds the end of arm 116 above the outer ratchet 114 until arm 116 is depressed, as shown in FIG. 7. In particular, a finger 124 pressing against resilient arm 116 causes arm 116 to extend underneath stop 118 so that the end 115 of arm 116 engages a detent in outer ratchet 114. This causes upper ring 90 to be rotated in a couterclockwise direction, as indicated by arrow 113.

A dog 120 acts as a detent in cooperation with inner ratchet 112 to prevent counterclockwise movement of upper ring 90 whenever actuator mechanism 110 is not in operation. Dog 120 is pivotally mounted at a point above upper ring support 84 and extends at the side thereof opposite ratchet 112 beneath arm 116. When arm 116 is depressed by finger 124, dog 120 is raised, thereby permitting upper ring 90 to be rotated in the afore described counterclockwise direction, arrow 113.

A corresponding dog, pivot, and resilient arm is provided in actuator mechanism 111 for causing clockwise rotation of upper ring 90. When upper ring 90 is rotated in a clockwise direction by actuator mechanism 111, dog 120 is raised by the ramp-like surface of inner ratchet 112 and then dropped into the next succeeding detent. Accordingly, the operator can selectively control the constrictive action of artificial sphincter 80 so as to either open or close a section of an organ passing through lumen 102. Furthermore, since artificial sphincter 80 is specifically configured to be implanted in a body with actuator mechanisms 110 and 111 beneath the outer skin surface, the operator can selectively open or close artificial sphincter 80 as desired.

Figure 8:
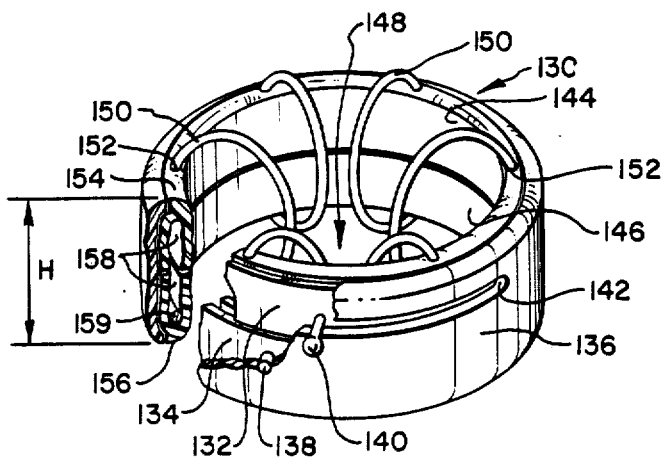
FIG. 8 is a perspective view of major components of yet another embodiment of an artificial sphincter according to the present invention in which some components have been broken away to reveal internal details.

Depicted in FIG. 8 is yet another embodiment of an artificial sphincter 130 of improved design and capable of gently constricting a living tissue conduit such that a flow of biological materials therewithin may be controlled without causing significant pressure and necrosis to the living tissue of the conduit.

Artificial sphincter 130 is composed of a first planar ring 132 secured adjacent to a second planar ring 134 by an alignment ring 136 which encircles the outer circumference of rings 132, 134. Second planar ring 134 is secured from rotation relative to alignment ring 136 by a set pin 138 which passes through alignment ring 136 and is embedded in second planar ring 134. First planar ring 132, however, is free to rotate relative second planar ring 134 and alignment ring 136 about an axis which coincides with that of second planar ring 134 and alignment ring 136.

In the embodiment of an artificial sphincter according to the present invention, the impetus to rotate first planar ring 132 is applied thereto through an actuator pin 140 rigidly attached to first planar ring 132 and projecting radially outwardly therefrom through a circumferentially elongated slate 142 formed in alignment ring 136. Actuator pin 140 is driven selectively in either direction within circumferentially elongated slot 142 by any one of a number of embodiments of an actuator means to be described subsequently.

First planar ring 132 contains a central opening 144 which has a diameter adequate at least to encircle the living tissue conduit (not shown) through which the flow of biological materials is to be controlled when a maximum desired volume of such biological material is flowing. The central opening 146 in second planar ring 134 is of a diameter equal to that of opening 144; although, as suggested in reference to the embodiment already described, this need not always be the case. Openings 144, 146 together generally define a passageway 148 for encircling the living tissue conduit to be subjected to the constrictive action of artificial sphincter 130. First and second planar rings are preferably made of a biocompatible material.

In accordance with one aspect of the present invention, an artificial sphincter for gently constricting a living tissue conduit, such as artificial sphincter 130, is provided with a closure means attached to the first and second planar rings of the device for radially narrowing a passageway therethrough, such as passageway 148. The closure means of the present invention gently constricts the living tissue conduit therein with a combination of rotational and circumferentially localized discrete radially compressive forces when the first planar ring is rotated in a predetermined direction relative the second planar ring.

As shown in FIG. 8, a plurality of tie members 150, shown by way of example to be six in number, extend between attachment locations on first planar ring 132 and second planar ring 134. The opposite ends of each of tie members 150 are secured within attachment apertures 152 formed in the nonadjacent faces 152, 154 of first and second planar rings 132, 134, respectively. Advantageously, attachment apertures 152 open into continuous recesses 158 formed within each of first and second planar rings 132, 134.

By employing continuous recesses 158 all tie members 150 may be formed from a single continuous length of material 159 which is threaded through attachment apertures 152 and continuous recess 158 until all tie members 150 have been formed. Only the two ends of the continuous length of material 159 need then be secured within continuous recesses 158 against removal through attachment apertures 152. This may be accomplished through any number of conventional means including gluing of the two ends of continuous length of material 159 or forming enlarged portions thereat through knotting, or preferably thermal forming. Tie members 150 thus formed of a single length of material will additionally have the advantageous capacity to automatically assume equal lengths and absorb equal tensions as artificial sphincter 130 is operated. Tie members 150 are preferably soft hollow flexible tubes comprised of a medical grade of polyurethane.

The action of tie members, such as tie members 150, in a collectively narrowing passageway, such as passageway 148, upon rotation of one of the two planar rings to which tie members are attached has been described somewhat above. Nevertheless, FIGS. 9A through 9D provide additional understanding of this process. In this set of figures, a specific tie member 150a and specific attachment aperture 152a have been designated for reference purposes, and first planar ring 132 has been rotated by successive increments relative to alignment ring 136 (and second planar ring 134 which is not visible) in the direction of arrow A.

Figure 9A:
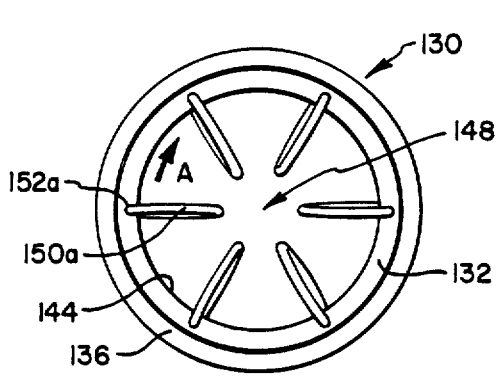
FIGS. 9A-9D are a sequence of plan view of the device of FIG. 8 illustrating operation of that device.
Figure 9B:
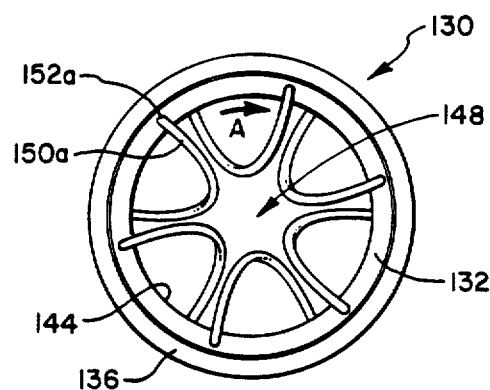

In FIG. 9A, tie member 150a forms a substantially vertical loop as the attachment locations of its opposite ends on each of first and second planar rings 132, 134, respectively, which are aligned vertically. Rotation of first ring 132 in the direction of arrow A, however, proceeds to separate the attachment locations for tie member 150a horizontally, thereby moving attachment aperture 152a in a clockwise direction and straightening out tie member 150a. A first stage of such rotation is illustrated in FIG. 9B.

Figure 9C:
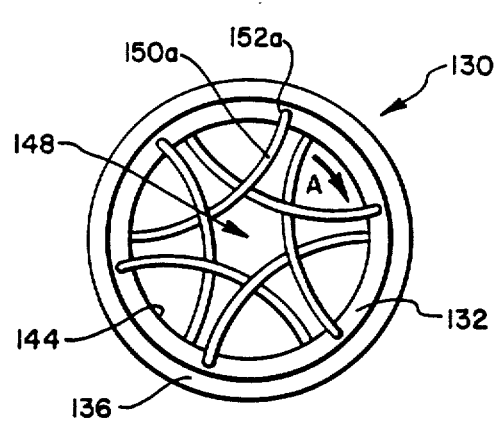

Additional rotation of first planar ring 132 in the same direction continues the process of straightening out tie member 150a which is begun to be drawn laterally toward the center of passageway 148, as shown in FIG. 9C. Ultimately, continued rotation of first planar ring 132 in the direction of arrow A will draw each of the tie members, such as tie member 150a, laterally into the center of the device completely closing passageway 148, as is shown in FIG. 9D.

Figure 9D:
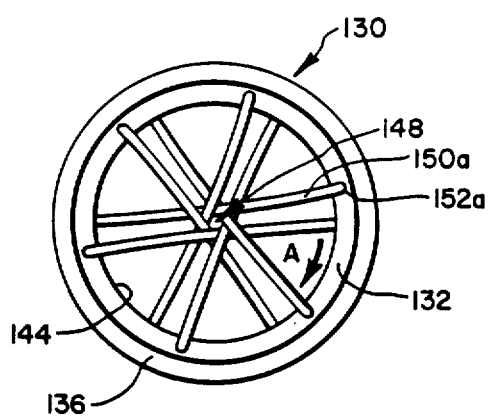

In practical terms, however, the degree of constriction depicted in FIG. 9D may never be required in operation of the device of the present invention. In gently gathering inwardly the walls of a living tissue conduit in passageway 148, each of the tie members asserts discrete radially-directed compressive forces upon the outer walls of the conduit. The tissue of those walls is accordingly urged into the opening within the conduit, thereby blocking that opening short of the degree of constriction shown in FIG. 9D.

Second, in addition to involving compressive forces as just described, it must be emphasized that the constricting action of an artificial sphincter, such as artificial sphincter 130, also imparts to the living tissue conduit a rotational force which serves to twist the living tissue conduit upon itself. This rotational force results from the geometry of artificial sphincter 130, in that the tie members, such as tie member 150a, even when fully outstretched are still inclined. Attachment apertures 152 formed on nonadjacent faces 154, 156 on first and second planar rings 132, 134, respectively, are separated at all times during rotation of first planar ring 132 by a vertical distance H (shown in FIG. 8) representing the height of artificial sphincter 130.

Thus, in the progressive closure depicted in FIGS. 9A through 9D, as the tie members begin to contact a living tissue conduit within passageway 148, they apply localized, discrete, radially compressive forces along lines which are inclined relative the axis of passageway 148 in the direction of rotation of first planar ring 132. As that rotation continues, the radially compressive effect of the drawing of tie members laterally toward the center of passageway 148 not only increases, but the tie members also obtain a degree of purchase upon the living tissue conduit and twist the conduit in the direction of rotation of first planar member 132.

This twisting motion is twofold in nature. First, because the upper ends of the tie members, such as tie members 150a, rotate with first planar ring 132, the grip collectively asserted by those tie members results in a mild twisting of living tissue conduit about its longitudinal axis. In addition, rotation of first planar ring 132 in the direction which results in closure of passageway 148 serves to increasingly separate the attachment locations at each end of the tie members to first and second planar rings 132 and 134.

Given that the vertical separation of the attachment locations at each end of any given tie member remains constant at H, the increasing separation of the attachment locations for each tie member imply that the inclination of each of the tie members is reduced as the first planar ring is rotated. When the tie members have contacted the conduit and begun to exerted a degree of purchase there upon, continued narrowing of the passageway by the closure means of the present invention also tends to draw opposite ends of the conduit inwardly toward the artificial sphincter in a unique closing action. Thus, the closure means of the disclosed invention can be seen to apply to living tissue conduit in passageway 148 a combination of rotational and radially directed compressive forces which uniquely imitate the natural action of sphincter-type muscle. A second embodiment of a closure means which performs this same unique action will be described presently below.

In accordance with the present invention, an artificial sphincter, such as artificial sphincter 130, is also provided with a cell-impervious means for enveloping first and second planar rings and the plurality of tie members to isolate those elements from the surrounding environment. This is essential for any device implanted on a long-term basis, as the intrusion of tissue growth among the moving parts of such a device could predictably be expected to preclude its successful functioning for any significant amount of time.

By way of example and not limitation, shown in FIG. 10 is a thin flexible tubular membrane 160 suitable to such long-term use. Tubular membrane 160 can, however, best be understood by reference first to its method of fabrication which preferably utilizes an hour-glass shaped mandrel 162 having a medial stem portion 164 with substantially cylindrical walls 166. The diameter of cylindrical walls 166 corresponds approximately to the diameter of passageway 148 through artificial sphincter 130. At either end of stem portion 164 are first and second radially enlarged bell portions 168, 170, respectively. The diameter of enlarged bell portions 168, 170 corresponds approximately to the diameter of the outer circumference of the artificial sphincter, such as artificial sphincter 130.

According to one aspect of method fabricating a thin flexible membrane including within the present invention, portion 164 and first and second bell portions 168, 170, respectively, are discrete components of mandrel 162. These are held together for nondestructive disassembly by threaded shafts 172 which pass through eyes 174 in first and second bell portions 168, 170, respectively, and cooperatively engage threads in central bore 176 in stem portion 164.

Further, according to the present invention, cylindrical walls 166 of stem portion 164 are provided with a plurality of parallel folds 178, each of which traverses the length of end portion 164. The longitudinal axes of folds 178 are inclined relative the axis of stem portion 164 in a direction which corresponds to the direction of rotation of planar ring 132 in relation to alignment ring 136 and second planar ring 134 predetermined to effect radial narrowing of passageway 148.

An example of a method for fabricating a thin membrane predetermined thickness, such as tubular membrane 160, is described below. In the preferred embodiment, tubular membrane 160 made of a biocompatible medical grade of polyurethane such as that sold under the name Tecoflex TM by Thermedics, Inc. This product is a solution grade polyurethane, 80 Shore A hardness, which is supplied in pellet form. The polyurethane can be made radio-opaque for testing purposes by the addition of a radio-opaque material, such as bismuth carbonate, after the polyurethane has been dissolved. Tecoflex TM polyurethane is a thermoplastic. Therefore the use of steam or dry heat is not recommended for sterilization. Tecoflex TM polyurethane may instead be sterilized using conventional ethylene oxide or radiation methods.

After constructing a mandrel of desired shape, such as mandrel 162, a solution of Tecoflex TM polyurethane must be prepared. Since this material is hygroscopic, the pellets of Tecoflexs TM should first be dried in a vacuum or in a circulating oven at 75° C. for five hours and then placed in a clean glass beaker with the appropriate quantity of methylene chloride needed to achieve six percent (6%) by weight solution of 80 A Tecoflex TM. The beaker should be covered to prevent evaporation, and the solution stirred at room temperature using a magnetic stirrer for twenty-four 24 hours.

A suitable mandrel, such as mandrel 162, is then dipped in the solution of polyurethane to apply a coating thereto. Introduction into the solution and removal therefrom should be accomplished gradually at approximately the rate of 1 inch per second. All bubbles in the resulting coating should be immediately wiped away as the mandrel is withdrawn from the solution. Mandrel 162 should be slightly larger than the size of tubular membrane 160 actually desired, since the product of this process will be approximately 5% smaller than the size of the mandrel upon which it is formed. Mandrel 162 should be cleaned with acetone prior to its first dipping, and all equipment that comes in contact with the solution or its vapors should be made of materials which are not affected by methylene chloride.

After obtaining a coating of polyurethane solution on mandrel 162, it is left to air dry for at least thirty 30 minutes. A single layer of polyurethane is having a thickness of approximately 0.001 inch will be deposited with each dip. To aggregate the desired thickness of material on the mandrel, alternate dipping and drying according to the instructions above are continued. Once the desired thickness is obtained, the coated mandrel should be left to aerate for twenty-four 24 hours prior to handling.

After the coating has dried, a portion thereof on end faces 180 of mandrel 162 are cut away, and tubular membrane 160 can be carefully removed and inspected for defects. The process of removing tubular membrane 160 from mandrel 162 is greatly facilitated by the disassembly of a mandrel 162 into its component parts, as shown in FIG. 11.

As seen in FIG. 12, tubular membrane 160 has a central waist portion 182 which is dimensioned to fit within openings, such as openings 144, 146, in the planar rings of artificial sphincter 130. The walls of waist portion 182, when inserted into artificial sphincter 130, define in a non-rigid manner a passageway, such as passageway 148, for receiving a living tissue conduit through which a flow of biological materials is to be controlled.

The walls of waist portion 182 of tubular membrane 160 are formed into a plurality of compliant folds 184. In the embodiment depicted in FIG. 12, compliant folds 184 have the longitudinal axes thereof inclined relative the axis of tubular membrane 160 in the direction of rotation of first planar ring 132 relative second planar ring 134 predetermined to effect radial narrowing of passageway 148. At each end of waist portion 182 are first and second radially flared portions 186, 188, respectively, which terminate in cut edges 190.

To assemble tubular membrane 160 about an artificial sphincter, such as artificial sphincter 130, either of first or second radially flared portions 186, 188, respectively, is inserted through openings 144, 146 in first and second planar rings 132, 134, respectively, so that waist portion 182 rests in passageway 148. Thereafter, first and second radially flared portions 186, 188 are folded outwardly over first and second planar rings 132, 134, so that cut edges 190 of first and second radially flared portions 186, 188, respectively, meet beyond the outer circumference of artificial sphincter 130. First and second radially flared portions 186, 188 are then sealed to each other using the solution from which tubular membrane 160 was fabricated at a seam 192, as shown in FIGS. 13A–13D. Membrane 160 as thus sealed about artificial sphincter 130 has a generally torodial configuration. When employed with a split-ring embodiment of an artificial sphincter, such as was shown and described in relation to FIG. 4, tubular membrane 160 must correspondingly be split parallel the axis of that toroid axis and resealed after encirclement of a living tissue conduit by the device.

Figure 14:
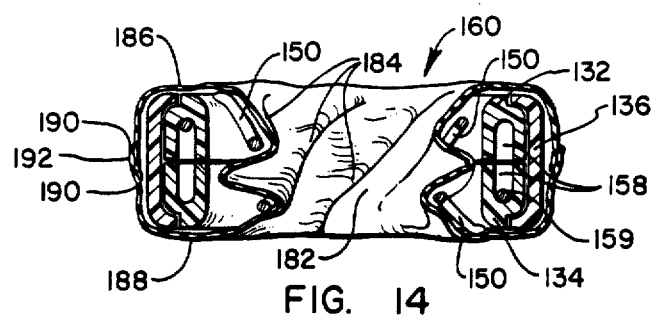
FIG. 14 is a sectional plan view taken along line 14—14 of FIG. 13C.

An understanding of the resultant structure is better acquired by reference to FIG. 14 in which tie members 150, first and second planar rings 132, 134, respectively, and alignment ring 136 can be seen in cross-section enveloped in tubular membrane 160. In this manner, the components within tubular membrane 160 may be insulated from the surrounding environment.

Compliant folds 184 in the walls of waist portion 182 serve a number of functions. As has been mentioned above in relation to FIG. 6, a straight, tube-like waist portion in an enclosure membrane for an artificial sphincter of the type disclosed herein is afflicted with both mechanical and medical inadequacies. First, constriction of a waist portion 101 defining a lumen 102 causes stretching of the membrane in the area between upper ring 90 and lower ring 86. This not only necessitates the application of unnecessary force to constrict lumen 102, but it also tends through continued long-term use to fatigue membrane 100, leading to early failure.

In addition, it has been discovered that constriction of a lumen within the waist portion of a membrane, such as membrane 100, does not permit each of the tie members 54 shown in FIG. 6 to individually apply rotational and radially compressive forces against the living tissue conduit within the lumen. Instead, the straight walls of waist portion 101 of membrane 100 act upon the living tissue conduit as a single circular ring-like pattern of pressure, tending to cut off circulation in the living tissue of the conduit.

These inadequacies are remedied, however, through the provision of a plurality of compliant folds, such as folds 184 which are configured according to the present invention. In the first instance, compliant folds 184 permit a limited amount of rotation of first radially flared portion 186 of tubular membrane 160 relative second radially flared portion 188 thereof without producing significant tension in the walls of waist portion 182. This permits opposite ends of tubular membrane 160 to rotate slightly with the underlying components of artificial sphincter 130 as constriction of passageway 148 is effected. Rotation of first planar ring 132 in the direction intended to produce radial narrowing of passageway 148 draws each of tie members 150 laterally toward the center of passageway 148 and into one of the plurality of compliant folds 184 in waist portion 182 of tubular membrane 160.

The extra material in each of complaint folds 184 thus permits lateral movement of tie members 150 without stretching membrane 160. Once within compliant folds 184, rotating tie members 150 tend to induce relative rotation of the opposite ends of tubular member 160, which is accommodated without producing significant tension in the walls of waist portion 182. Compliant folds 184 in addition provide additional pleats of material in the walls of waist portion 182, whereby narrowing of passage way 148 may be accomplished without stretching. Thus, tubular membrane 160 ultimately participates with tie members 150 radially narrowing passageway 148 and gently constricting the living tissue conduit therewithin through the application of a combination of rotational and circumferentially localize discrete radially compressive forces.

FIGS. 13A-13D show the external appearance of an artificial sphincter enclosed in a tubular membrane, such as tubular membrane 160, and operated to effect radial narrowing of passsageway 148 in a manner corresponding FIGS. 9A-9D. In FIGS. 13A-13D, rotation of first planar ring 132 within tubular membrane 160 is in the direction indicated by arrow A. As can be observed, that rotation produces radially narrowing of passageway 148 which is effected by edges of each of folds 184 radially innermost to passageway 148.

Figure 15:
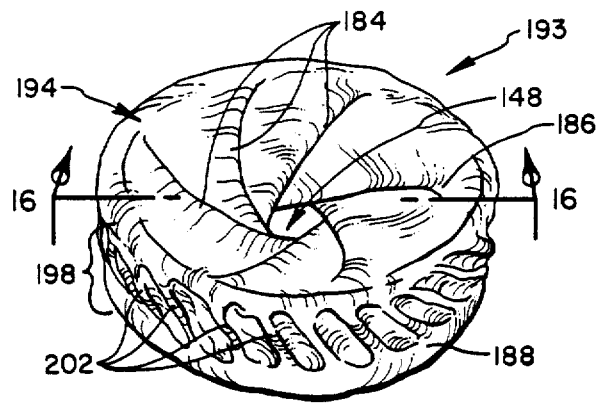
FIG. 15 is a perspective view of yet another embodiment of an artificial sphincter according to the present invention.

The realization of these significant advantages in a tubular membrane for enveloping an artificial sphincter have permitted development of yet another embodiment of an artificial sphincter embodying the teachings of the present invention. Shown in FIGS. 15 and 16 is a simplified thin-profile artificial sphincter 193 having great promise for use as a urinary-tract sphincter.

Artificial sphincter 193 is provided with a flexible tubular membrane, similar to thin membrane 160, which functions as a closure means for radially narrowing passageway 148 in addition to isolating components within the membrane from the surrounding environment. Such an enhanced tubular membrane 194 is shown to include a central waist portion 182 with walls which define a nonrigid manner passageway 148 for receiving a living tissue conduit. The walls of waist portion 182 are provided with a plurality of compliant folds 184 inclined relative the axis of passageway 148 in the direction of rotation of first planar ring 132 required to effect narrowing of passageway 148.

All these features are as those included in tubular membrane 160 shown in FIG. 14. By contrast, however, first radially flared portion 186 of enhanced tubular membrane 194 is secured by an adhesive 196 to nonadjacent face 154 of first planar ring 132. Correspondingly, second radially flared portion 188 of enhanced tubular membrane 194 is attached by adhesive 196 to nonadjacent face 156 of second planar ring 134.

Figure 16:
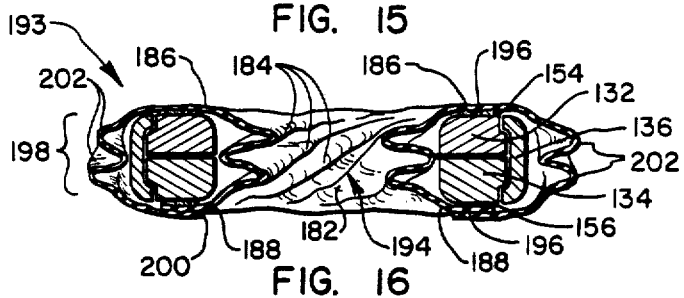
FIG. 16 is a sectional elevation view taken along line 16—16 of FIG. 15.

FIG. 16 reveals that artificial sphincter 193 is not, however, provided with a plurality of tie members, such as tie members 150, shown in the other embodiments of FIGS. 8 and 14. Nonetheless, rotation of first planar ring 132 relative second planar ring 134 in the direction indicated by arrow A in FIGS. 9A-9D produces the same radial narrowing of passageway 148 as is produced by tubular membrane 160, overlying a device that does include tie members.

If attached to first and second planar rings 132, 134 as described above, enhanced tubular membrane 194 functions equally well as a closure means for gently constricting a living conduit in passageway 148 by a combination of rotational and circumferentially localized discrete radial compressive forces. Thus, actuation of the device shown in FIGS. 15 and 16 outwardly resembles in most significant aspects the operation of the device shown in FIGS. 13A-13D, which included tie members 150.

Attachment of first radially flared portions 186, 188 to first and second planar rings 132, 134 for rotation therewith subjects the walls of enhanced tubular membrane 194, encircling the outer circumferential edges of the artificial sphincter, to stresses of the type which in the device of FIG. 6 stimulated inclusion of a plurality of compliant folds 184 in waist portion 182 of tubular membrane 160.

Accordingly, in another aspect of the present invention, a tubular membrane which is to function both as a closure means and as a cell-impervious means for enveloping an artificial sphincter, must be provided with means for enclosing the first and second planar rings for isolation from the surrounding environment. As shown in FIGS. 15 and 16, enhanced tubular membrane 194 includes a generally cylindrical portion 198 attached to first radially flared portion 186 at the end thereof opposite waist portion 186.

Generally cylindrical portion 198 is dimensioned such that the edge 200 of the walls thereof can extend around the outer circumference of the artificial sphincter and be sealed to second radially flared portion 188. Enhanced tubular membrane 194 as thus sealed about an artificial sphincter has a generally toroidal configuration. When employed with a split-ring embodiment of an artificial sphincter according to the present invention, enhanced tubular membrane 194 must correspondingly be opened parallel to the axis of that toroid and resealed after encirclement of the living tissue conduit by the device.

The walls of generally cylindrical portion 198 are in addition formed into a plurality of additional compliant folds 202, the longitudinal axes of which are inclined relative the axis of passageway 148 in the direction of rotation of first planar ring 132 required for radially narrowing passageway 148. Additional compliant folds 202 permit a limited amount of rotation of first radially flared portion 186 relative second radially flared portion 188 without producing significant tension in generally cylindrical portion 198.

The space interior to tubular membrane 160 or enhanced tubular membrane 194 can be filled with a fluid to assist in maintaining the integrity of the shape of the membrane. For example, it is advantageous that the shape of the inclined folds in the waist portion of such membranes be maintained in order to soften the purchase of compliant folds 184 on a living tissue conduit. As used herein, the term fluid is to be understood to include liquids in any form, as well as foams, gels, or gases.

Figure 17:
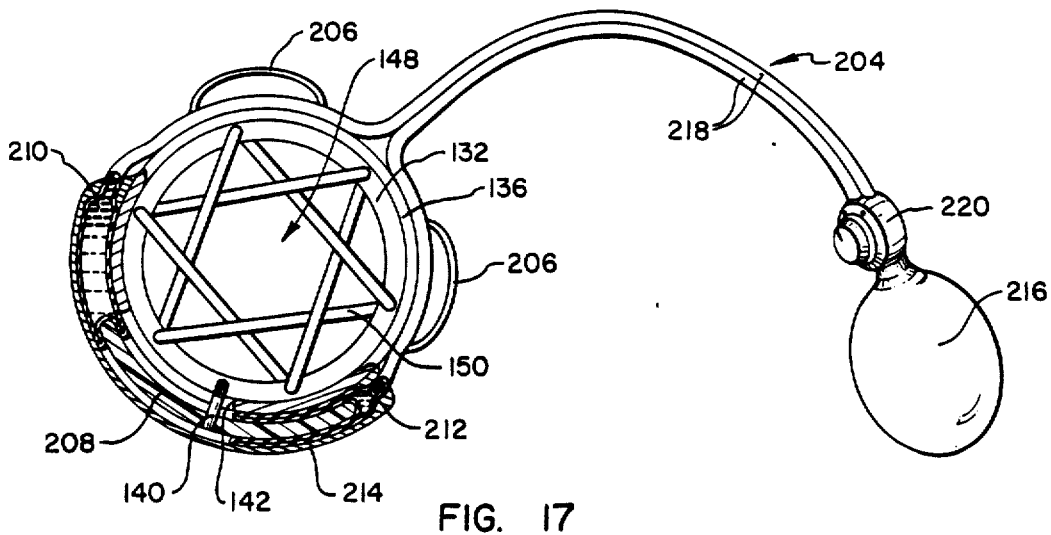
FIG. 17 is a plan view in partial section of a first means for actuating a device according to the present invention.

In yet another aspect of the present invention, actuator means are provided for rotating the first planar ring relative the second planar ring of an artificial sphincter in order to control narrowing and widening of a passageway therethrough. In FIG. 17, another embodiment of an artificial sphincter 204 is shown that includes suture rings 206 made of the same preferred hollow tubing as tie members 150. Suture rings 206 may be attached to alignment ring 136 or directly to second planar ring 134 to permit surgical anchoring of artificial sphincter 204 in a living organism. Suture rings 206 in combination with a set pin, such as set pin 138 shown in FIG. 8, afford means for securing second planar ring 134 relative passageway 148.

Artificial sphincter 204 includes a ram 208 attached to first planar ring 132 by actuator pin 140 for rotation with first ring 132. Reversible hydraulic drive means in the form of rolling hydraulic diaphragms 210, 212 housed in a curved casing 214 on the exterior circumference of alignment ring 136 drive rim 208 in either direction of rotation selectively. A hydraulic pressure bulb 216 remote from artificial sphincter 204 is connected to each of rolling hydraulic diaphragms 210, 212 by two hydraulic lines 218. The pressure generated in hydraulic pressure bulb 216 is selectively applied to one of hydraulic lines 218 by adjusting control switch 220. In the process, the corresponding rolling hydraulic diaphragm inflates, thereby pushing ram 208 and first planar ring 132 attached thereto forward circumferentially. The other rolling hydraulic diaphragm collapses as ram 208 moves thereinto.

Figure 18:
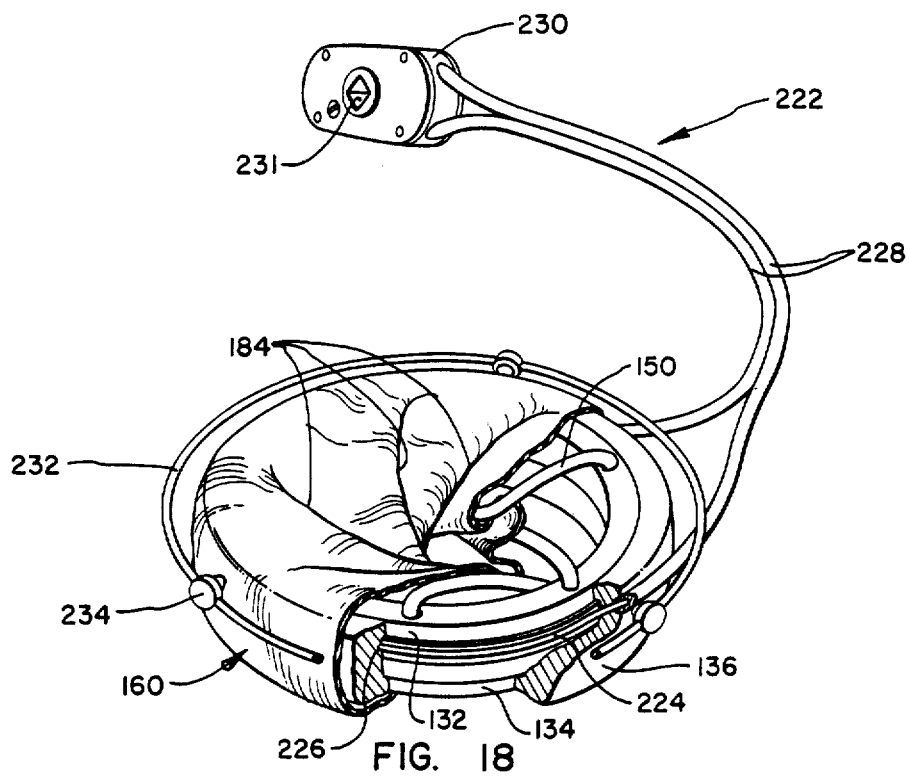
FIG. 18 is a partial break away perspective view of a second embodiment of an actuation means for a device according to the present invention.

Another embodiment of an artificial sphincter 222 employing an actuator means of a different type is shown in FIG. 18. Therein, a cable pulley actuator is shown which employs a continuous loop of filament 224 wrapped around and attached to first planar ring 132 within a circumferential groove 126 on the inner surface of alignment ring 136 to effect rotation of first planar ring 132. Filament 224 is operably connected within tubing 228 to a control means 230 remote from artificial sphincter 222. Rotation of ratchet receptacle 231 permits selective longitudinal motion of filament 224 in either direction and motion of first planar ring 132 accordingly.

Artificial sphincter 222 is provided with a second embodiment of a suture ring 232 for surgical anchoring of the device within a living organism. Suture ring 232 is attached to alignment ring 136 by posts 234 which pass through tubular membrane 160. Wherever such a penetration of the enclosing membrane occurs, either for suture ring attachment or for passage of connectors to a control means, the penetrating part is sealed to the tubular membrane using the polyurethane solution from which the membrane was fabricated.

Figure 19:
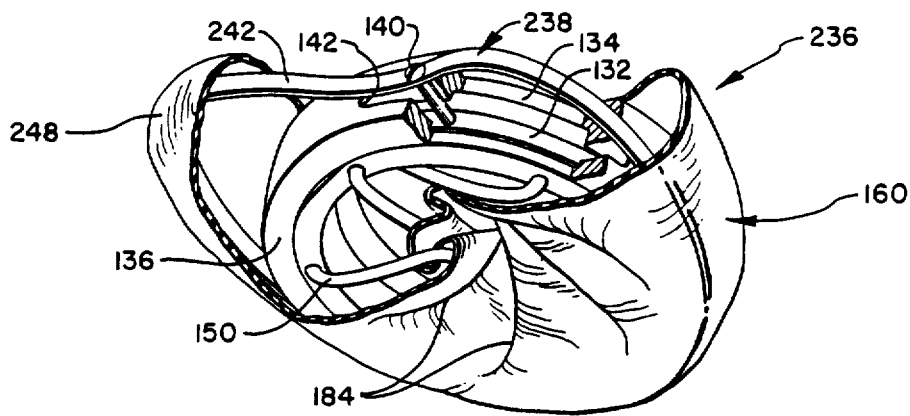
FIG. 19 is a partial break away perspective view of a third embodiment of an actuation means for use with a device according to the present invention.
Figure 20A:
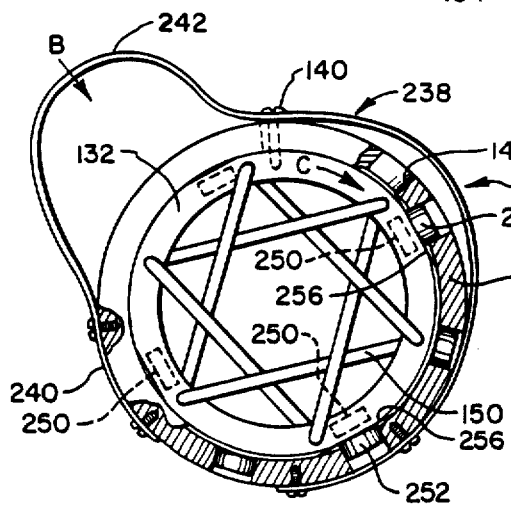
FIGS. 20A and 20B are partially broken away plan views of the device of FIG. 19 in two stages of operation.
Figure 20B:
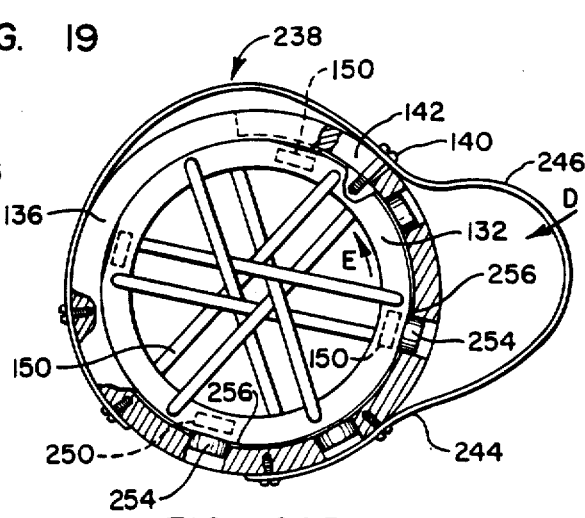

A final embodiment of an artificial sphincter 236 employing yet another actuator means shown in FIGS. 19, 20A, and 20B. A resilient strip 238 is attached at a medial position thereof by way of actuator pin 140 to first planar ring 132 accordingly. As shown in FIG. 20A, one end 240 of resilient strip 238 is secured to alignment ring 136 such that the portion of resilient strip 248 between actuator pin 140 and end 238 is longer than the distance around the outer circumference of alignment ring 136 between the corresponding points of attachment of resilient strip 238 to artificial sphincter 236. Thus, resilient strip 238 between its points of attachment arches away from the device in a first control loop 242.

Forcing of first control loop 242 towards the device as shown by arrow B, rotates first planar ring 132 in the direction shown by arrow C. As shown in FIG. 20B, the other end 244 of resilient strip 238 is attached to alignment ring 136 in a corresponding manner to produce a second control loop 246. If second control loop 246 is forced toward the device in the direction shown by arrow D, first planar ring 132 rotates in a direction indicated by arrow E.

Unlike the actuator means shown in FIGS. 17 and 18, the actuation means shown in FIGS. 19 and 20A and 20B does not pass through tubular membrane 160. First and second control loops 242 and 246 are accommodated in appropriately dimensioned protuberances 248 provided on tubular membrane 160, and operation of the device is achieved through direct manipulation through the skin at the point of implantation.

In yet another aspect of the present invention, an artificial sphincter, such as artificial sphincter 236, is provided with an overridable locking means for securing the first planar ring relative the second planar ring in at least one preselected rotational position thereof. As shown in FIG. 20A, magnets 250 are housed within first planar ring 132 for rotation therewith. Housed within alignment ring 136 closely opposing magnet 250 in first planar ring 132, when first planar ring 132 is in a first preselected rotational position, are first location determining magnets 252. The mutual attraction of magnets 250 and first location determining magnets 252 tends to hold first planar ring 132 in the first preselected rotational position until force of rotation in excess of that mutual magnetic attraction is applied to first planar ring 132.

As further shown in FIG. 20B, second location designating magnets 254 are housed in alignment ring 136 closely opposing magnets 250 when first planar ring 132 is in a second preselected rotational position. Similarly, mutual attraction of magnets 250 and second location determining magnets 254 will hold first planar ring 132 in the second preselected rotational position until force in excess of that mutual attraction is applied to first planar ring 132.

To assist in this locking action, the outer circumference of first planar ring 132 at the location of each of magnets 150 formed into a radially inwardly flattened portion 256. First and second location determining magnets 252, 254, respectively, are housed in location designating magnet apertures 258. Location designating apertures 258 permit, for example, first location designating magnets 252 to be drawn radially inwardly by the attraction of magnets 250 so as to bear against flattened portion 256 on the outer circumference of first planar ring 132 when first planar ring 132 is in the first preselected rotational position shown in FIG. 20A. This more securely locks first planar ring 132 in the first preselected rotational position. Second location determining magnets 254 function in a similar manner when first planar ring 132 is in the second preselected rotational position shown in FIG. 20B.

The several embodiments of an artificial sphincter described above embody an invention for constricting a living tissue conduit such that flow of biological materials within the living tissue conduit may be controlled without causing significant pressure necrosis to the living tissue of the conduit. In implanting any of the above-described embodiments in a patient, it is necessary to insert the living tissue conduit in which a flow of biological materials is to be controlled through the openings in the first and second planar rings, as well as through whatever closure means is attached to the first and second planar rings for radially narrowing the passageway defined by the rings. In instances where surgical severance of the living tissue conduit should not be undertaken, an embodiment of the invention is employed utilizing rings that can be opened at their circumference and reclosed about the living tissue conduit. Thereafter, the device is surgically anchored within the body of the patient, and actuator means are provided for rotating first planar ring relative the second planar ring to control narrowing and widening of the passageway in which the living tissue conduit has been inserted.

From the descriptions above, it can be understood that the artificial sphincter and method of the present invention are capable of gently constricting a living tissue conduit such that flow of biological materials therewithin may be controlled without causing significant pressure necrosis to the living tissue of the conduit. This is accomplished using a plurality of ties or a specially shaped thin enclosure membrane either of which is attached to two coaxially rotating rings that encircle the conduit. When one ring is rotated relative the other, the ties or membrane constrict the living tissue conduit with a combination of rotational and circumferentially localized discrete radially compressive forces which do not harm the tissue of the conduit.

In addition, the artificial sphincter of the present invention is rendered suitable for implantation by being isolated from the surrounding environment is a cell-impervious membrane which prevents cell intrusion into the device. Operative mechanisms of the artificial sphincter disclosed herein can be activated through direct manipulation of the implanted device or through use of a number of control means remote from the site of the implantation.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and intended to be secured by Letters Patent is:

1. An artificial sphincter for gently constricting a living tissue conduit such that flow of biological materials within the living tissue conduit may be controlled without causing significant pressure necrosis to the living tissue of the conduit, the artificial sphincter comprising:
   a first planar ring having an opening with a diameter adequate to at least encircle the living tissue conduit when a maximum desired flow of biological materials is passing therethrough;
   a second planar ring having an opening with a diameter greater than or equal to the diameter of the opening of the first planar ring, said second planar ring being positioned in close proximity to the first planar ring to permit coaxial rotation of the first planar ring relative the second planar ring, the openings in the first and second planar rings generally defining a passageway for encircling the living tissue conduit; and
   closure means attached to the first and second planar rings for radially narrowing the passageway and gently constricting the living tissue conduit with a combination of rotational and circumferentially localized discrete radially compressive forces upon rotation of the first planar relative the second planar ring.

2. An artificial sphincter for gently constricting a living tissue conduit as defined in claim 1, wherein the first and second planar rings are positioned adjacent one another.

3. An artificial sphincter for gently constricting a living tissue conduit as defined in claim 1, wherein the first and second planar rings may be split at the circumference thereof for receiving the living tissue conduit in the openings in the first and second planar rings.

4. An artificial sphincter for gently constricting a living tissue conduit as defined in claim 2, wherein the first and second planar rings are comprised of a biocompatible material.

5. An artificial sphincter for gently constricting a living tissue conduit as defined in claim 1, wherein the closure means comprises a plurality of tie members, each of said tie members extending between an attachment location on the first planar ring and an attachment location on the second planar ring, so that rotation of the first planar ring relative the second planar ring draws the tie members laterally toward the center of the passageway radially narrowing the passageway.

6. An artificial sphincter for gently constricting a living tissue conduit as defined in claim 5, wherein the tie members are hollow, flexible tubes.

7. An artificial sphincter for gently constricting a living tissue conduit as defined in claim 6, wherein the tie members are comprised of medical grade polyurethane.

8. An artificial sphincter for gently constricting a living tissue conduit as defined in claim 5, wherein an attachment aperture for securing opposite ends of each of the tie members is formed in the first and second planar rings at each of the attachment locations.

9. An artificial sphincter for gently constricting a living tissue conduit as defined in claim 8, wherein the attachment apertures formed in the first and second planar rings open onto a continuous recess formed within each of the first and second planar rings, and the tie members are segments of a single length of flexible material threaded through the attachment apertures and the continuous recesses.

10. An artificial sphincter for gently constricting a living tissue conduit as defined in claim 1, wherein the closure means comprises a thin flexible tubular membrane, the membrane comprising:

a central waist portion dimensioned to fit within the openings of the first and second planar rings and having walls for defining in a nonrigid manner the passageway for receiving the living tissue conduit; and first and second radially flared portions at each end of the waist portion, the first and second flared portions extending outwardly and being secured to the first and second planar rings respectively, such that when the waist portion resides within the openings of the first and second rings, rotation of the first planar ring relative the second planar ring produces radial narrowing of the channel by the walls of the waist portion of the membrane.

11. An artificial sphincter for gently constricting a living tissue conduit as defined in claim 10, wherein the walls of the waist portion of the membrane are formed into a plurality of compliant folds for permitting a limited amount of rotation of the the first radially flared portion relative the second radially flared portion without producing significant tension in the walls of the waist portion.

12. An artificial sphincter for gently constricting a living tissue conduit as defined in claim 11, wherein the longitudinal axis of each of the compliant folds is inclined relative the axis of the passageway at a preselected angle in a predetermined direction of rotation of the first planar ring relative the second planar ring, and wherein the edges of each of the folds radially innermost to the passageway effect narrowing thereof.

13. An artificial sphincter for gently constricting a living tissue conduit as defined in claim 12, wherein the membrane encloses a quantity of fluid to assist in maintaining the integrity of the shape of the membrane.

14. An artificial sphincter for gently constricting a living tissue conduit as defined in claim 12, wherein the membrane further comprises means for enclosing the first and second planar rings within the membrane to isolate the first and second planar rings from the surrounding environment.

15. An artificial sphincter for gently constricting a living tissue conduit as defined in claim 14, wherein the means for enclosing the first and second planar rings within the membrane comprises a generally cylindrical portion of the membrane attached to the first radially flared portion at the end thereof opposite the waist portion, the generally cylindrical portion having walls for encircling the outer circumferential edges of the first and second planar rings.

16. An artificial sphincter for gently constricting a living tissue conduit as defined in claim 15, wherein the generally cylindrical portion of the membrane is dimensioned such that the end of the walls thereof opposite the first radially flared portion can be sealed to the second radially flared portion to isolate the first and second planar rings from the surrounding environment when the walls of the generally cylindrical portion encircle the outer circumference of the first and second planar rings.

17. An artificial sphincter for gently constricting a living tissue conduit as defined in claim 16, wherein the walls of the generally cylindrical portion of the membrane are formed into a plurality of compliant folds for permitting a limited amount of rotation of the first radially flared portion relative the second radially flared portion without producing significant tension in the generally cylindrical portion.

18. An artificial sphincter for gently constricting a living tissue conduit as defined in claim 17, wherein the longitudinal axis of each of the folds in the walls of the generally cylindrical portion of the membrane is inclined relative the axis of the passageway at a preselected angle in the predetermine direction of rotation of the first planar ring relative the second planar ring.

19. An artificial sphincter for gently constricting a living tissue conduit as defined in claim 16, wherein the thin flexible tubular membrane is cell impervious.

20. An artificial sphincter for gently constricting a living tissue conduit as defined in claim 19, wherein the thin flexible tubular membrane is comprised of medical grade polyurethane.

21. An artificial sphincter for gently constricting a living tissue conduit as defined such that flow of biological materials within the living tissue conduit may be controlled without causing significant pressure necrosis to the living tissue of the conduit, the artificial sphincter comprising:

a first planar ring having an opening with a diameter adequate to at least encircle the living tissue conduit when a maximum desired flow of biological materials is passing therethrough;

a second planar ring having a central opening with a diameter greater than or equal to the diameter of the central opening of the first planar ring, the second planar ring being positioned in close proximity to the first planar ring to permit coaxial rotation of the first planar ring relative the second planar ring, the openings in the first and second planar rings generally defining a passageway for encircling the living tissue conduit;

a plurality of tie members attached to the first and second planar rings for radially narrowing the passageway and gently constricting the living tissue conduit with a combination of rotational and circumferentially localized discrete radially compressive forces upon rotation of the first planar ring relative the second planar ring; and a cell impervious means for enveloping the first and second planar rings and the plurality of tie members to isolate the first and second planar rings and the plurality of tie members from the surrounding environment.

22. An artificial sphincter for gently constricting a living tissue conduit as defined in claim 21, wherein the cell impervious means comprises a thin flexible tubular membrane, the membrane comprising:

a central waist portion dimensioned to fit within the openings of the first and second planar rings and having walls for defining in a nonrigid manner the passageway for receiving the living tissue conduit; and radially flared portions at each end of the waist portion, the radially flared portions extending outwardly such that when the waist portion is inserted within the openings in the first and second planar rings, the radially flared portions may be sealed to each other exterior the first and second planar rings and the plurality of tie members.

23. An artificial sphincter for gently constricting a living tissue conduit as defined in claim 22, wherein the walls of the waist portion of the membrane are formed into a plurality of compliant folds for permitting a limited amount of rotation of the first radially flared portion relative the second radially flared portion without producing significant tension in the walls of the waist portion of the membrane.

24. An artificial sphincter for gently constricting a living tissue conduit as defined in claim 23, wherein the longitudinal axis of each of the compliant folds is inclined relative the axis of the passageway at a preselected angle in a predetermined direction of rotation of the first planar ring relative the second planar ring.

25. An artificial sphincter for gently constricting a living tissue conduit as defined in claim 24, wherein rotation of the first planar ring in the predetermined direction relative the second planar ring draws the tie members laterally toward the center of the passageway and into individual ones of the plurality of compliant folds in the waist portion of the membrane.

26. An artificial sphincter for gently constricting a living tissue conduit as defined in claim 1, further comprising an alignment ring for encircling the outer circumference of the first and second planar rings to secure the first and second planar rings in close proximity to each other and permit coaxial rotation of the first planar ring relative the second planar ring.

27. An artificial sphincter for gently constricting a living tissue conduit as defined in claim 26, further comprising at least one suture ring attached to the alignment ring for surgically anchoring the artificial sphincter within a living organism.

28. An artificial sphincter for gently constricting a living tissue conduit as defined in claim 1, further comprising at least one suture ring attached to the second planar ring for surgically anchoring the artificial sphincter within a living organism.

29. An artificial sphincter for gently constricting a living tissue conduit such that flow of biological materials within the living tissue conduit may be controlled without causing significant pressure necrosis to the living tissue of the conduit, the artificial sphincter comprising:

a first planar ring having an opening with a diameter adequate to at least encircle the living tissue conduit when a maximum flow of biological materials is passing therethrough;

a second planar ring having an opening with a diameter greater than or equal to the diameter of the opening of the first planar ring, the second planar ring being positioned in close proximity to the first planar ring to permit coaxial rotation of the first planar ring relative the second planar ring, the openings in the first and second planar rings generally defining a passageway for encircling the living tissue conduit;

closure means attached to the first and second planar rings for radially narrowing the passageway and gently constricting the living tissue conduit with a combination of rotational and circumferentially localized discrete radial compressive forces upon rotation of the first planar ring relative the second planar ring; and actuator means for rotating the first planar ring relative the second planar ring to control narrowing and widening of the passageway for receiving the living tissue conduit.

30. An artificial sphincter for gently constricting a living tissue conduit as defined in claim 29, wherein the actuator means comprises:

means for securing the second planar ring relative the passageway for receiving the living tissue conduit;

a cable attached to the first ring; and control means remote from the first ring and operably connected with the cable for selectively effecting reversible longitudinal motion of the cable.

31. An artificial sphincter for gently constricting a living tissue conduit as defined in claim 30, wherein the means for securing the second planar ring relative the passageway for receiving the living tissue conduit comprises at least one suture ring secured in fixed relationship to the second planar ring for surgically anchoring the artificial sphincter within a living organism.

32. An artificial sphincter for gently constricting a living tissue conduit as defined in claim 29, wherein the actuator means comprises:

means for securing the second planar ring relative the passageway for receiving the living tissue conduit;

a ram attached to the first ring for rotation therewith;

reversible hydraulic drive means for moving the ram; and control means remote from the reversible hydraulic drive means and operably connected thereto for selectively effecting reversible movement of the ram.

33. An artificial sphincter for gently constricting a living tissue conduit as defined in claim 32, wherein the means for securing the second planar ring relative the passageway for receiving the living tissue conduit comprises at least one suture ring secured in fixed relationship to the second planar ring for surgically anchoring the artificial sphincter within a living organism.

34. An artificial sphincter for gently constricting a living tissue conduit as defined in claim 29, wherein the actuator means comprises:

means for securing the second planar ring relative the channel for receiving the living tissue conduit; and a first resilient strip attached at a first point thereof to a first point on the first planar ring and at a second point thereof to a first point having a fixed relationship to the second planar ring, the length of the first resilient strip between the first and second points thereon exceeding the distance between the first point on the first planar ring and the first point having a fixed relationship to the second planar ring, such that the first resilient strip arches away from the first and second planar rings in a first control loop and forcing of the first control loop toward the first and second planar rings rotates the first planar ring relative the second planar ring in a first direction which carries the first point on the first planar ring circumferentially away from the first point having a fixed relationship to the second planar ring.

35. An artificial sphincter for gently constricting a living tissue conduit as defined in claim 34, wherein the actuator means further comprises a second resilient strip attached at a first point thereof to a second point on the first planar ring and at a second point thereon to a second point having a fixed relationship to the second planar ring, the length of the second resilient strip between the first and second points thereon exceeding the distance between the second point on the first planar ring and the second point having a fixed relationship to the second planar ring, so that the second resilient strip arches away from the first and second planar rings in a second control loop and forcing of the second control loop toward the first and second planar rings rotates the first planar ring relative the second planar ring in a second direction which carries the second point on the first planar ring circumferentially away from the second point having a fixed relationship to the second planar ring, the second direction of rotation of the first planar ring being opposite the first direction of rotation of the first planar ring.

36. An artificial sphincter for gently constricting a living tissue conduit as defined in claim 35, wherein:
  the first and second points on the first planar ring are identical;
  the first and second resilient strips are integrally formed with each other; and
  the first points on the first and second resilient strips are identical.

37. An artificial sphincter for gently constricting a living tissue conduit as defined in claim 36, further comprising an alignment ring for encircling the outer circumference of the first and second planar rings for securing the first and second planar rings in close proximity to each other and permitting relative coaxial rotation of the first planar ring relative the alignment ring and the second planar ring, and wherein the first and second points having a fixed relationship to the second planar ring are located on the alignment ring.

38. An artificial sphincter for gently constricting a living tissue conduit as defined in claim 37, wherein the means for securing the second planar ring relative the passageway for receiving the living tissue conduit comprises at least one suture ring secured in fixed relationship to the alignment ring for surgically anchoring the artificial sphincter within a living organism.

39. An artificial sphincter for gently constricting a living tissue conduit as defined in claim 34, wherein the means for securing the second planar ring relative the passageway for receiving the living tissue conduit comprises at least one suture ring secured in fixed relationship to the second planar ring for surgically anchoring the artificial sphincter within a living organism.

40. An artificial sphincter for gently constricting a living tissue conduit such that flow of biological materials within the living tissue conduit may be controlled without causing significant pressure necrosis to the living tissue of the conduit, the artificial sphincter comprising:
  a first planar ring having an opening with a diameter adequate to at least encircle the living tissue conduit when a maximum desired flow of biological materials is passing therethrough;
  a second planar ring having an opening with a diameter greater than or equal to the diameter of the opening of the first planar ring, the second planar ring being positioned in close proximity to the first planar ring to permit coaxial rotation of the first planar ring relative the second planar ring, the openings in the first and second planar rings defining a passageway for encircling the living tissue conduit;
  an alignment ring for encircling the outer circumference of the first and second planar rings for securing the first and second planar rings in close proximity to each other and permitting coaxial rotation of the first planar ring relative the second planar ring;
  closure means attached to the first and second planar rings for narrowing the passageway and gently constricting the living tissue conduit with a combination of rotational and circumferentially localized discrete radially compressive forces upon rotation of the first planar ring relative the second planar ring;
  actuator means for rotating the first planar ring relative the second planar ring to control narrowing and widening of the passageway for receiving the living tissue conduit; and
  an overridable locking means for securing the first planar ring relative the second planar ring in a preselected rotational position.

41. An artificial sphincter for gently constricting a living tissue conduit as defined in claim 40, wherein the overridable locking means for securing the first planar ring relative the second planar ring in a preselected rotational position comprises:
  at least one magnet housed within the first planar ring and rotatable therewith; and
  a first location determining magnet secured in a circumferentially fixed relationship to the second planar ring at a location closely opposing the magnet housed within the first planar ring when the first planar ring is in a first preselected rotational position so that movement of the first planar ring out of the first preselected rotational position overcomes the mutual attraction of the magnet housed in the first planar ring and the first location designating magnet.

42. An artificial sphincter for gently constricting a living tissue conduit as defined in claim 41, wherein the overridable locking means for securing the first planar ring relative the second planar ring in a preselected rotational position further comprises a second location designating magnet secured in a circumferentially fixed relationship to the second planar ring at a location closely opposing the magnet housed in the first planar ring when the first planar ring is in a second preselected rotational position, so that movement of the first planar ring out of the second preselected rotational position overcomes the mutual attraction of the magnet housed in the first planar ring and the second location designating magnet.

43. An artificial sphincter for gently constricting a living tissue conduit as defined in claim 42, wherein:
  the outer circumference of the first planar ring at the location of the magnet housed therewithin is formed into a radially inwardly flattened portion; and
  the interior circumference of the alignment ring is formed into a first location designating magnet aperture for housing the first location designating magnet and permitting the first location designating magent to be drawn toward the first planar ring by the magnet housed within the first planar ring to bear against the flattened portion thereof when the first planar ring is in the first preselected rotational position.

* * * * *

UNITED STATES PATENT AND TRADEMARK OFFICE
CERTIFICATE OF CORRECTION

PATENT NO. : 4,705,518

DATED : November 10, 1987

INVENTOR(S) : Charles D. Baker et al.

It is certified that error appears in the above-identified patent and that said Letters Patent is hereby corrected as shown below:

Column 1, line 48, "changes" should be --chances--
Column 1, line 67, "invention involve" should be --invention involves--
Column 6, line 25, "whould" should be --should--
Column 10, line 58, "sphincter-type muscle." should be --sphincter-type muscles.--
Column 13, line 55, "passage way" should be --passageway--
Column 13, line 60, "localize" should be --localized--
Column 13, lines 65-66, "corresponding" should be --corresponding to--
Column 14, line 1, "radially narrowing" should be --radial narrowing--
Column 16, line 20, "means shown" should be --means is shown--
Column 17, line 9, "150 formed" should be --150 is formed--
Column 17, line 62, "is a" should be --in a--
Column 19, line 34, delete the first occurrence of "the"
Column 20, line 20, "the predetermine direction" should be --the predetermined direction--

Signed and Sealed this

Twenty-eighth Day of June, 1988

Attest:

DONALD J. QUIGG

Attesting Officer

Commissioner of Patents and Trademarks